US 7,401,921 B2

(12) United States Patent
Baker et al.

(10) Patent No.: US 7,401,921 B2
(45) Date of Patent: Jul. 22, 2008

(54) MOTORIZED PATIENT SUPPORT FOR EYE EXAMINATION OR TREATMENT

(75) Inventors: Chris Baker, Moraga, CA (US); Kabir Arianta, Livermore, CA (US)

(73) Assignee: Carl Zeiss Meditec, Inc., Dublin, CA (US)

(*) Notice: Subject to any disclaimer, the term of this patent is extended or adjusted under 35 U.S.C. 154(b) by 595 days.

(21) Appl. No.: 10/843,767

(22) Filed: May 12, 2004

(65) Prior Publication Data

US 2005/0254009 A1 Nov. 17, 2005

(51) Int. Cl.
*A61B 3/00* (2006.01)
(52) U.S. Cl. ............................... 351/245; 351/246
(58) Field of Classification Search ............... 351/245
See application file for complete search history.

(56) References Cited

U.S. PATENT DOCUMENTS

| 3,475,075 A | 10/1969 | Stone, Jr. ............. 350/85 |
| 3,594,072 A | 7/1971 | Natick et al. .......... 351/38 |
| 4,128,317 A | 12/1978 | LeCover ............... 351/38 |
| 4,139,280 A | 2/1979 | Köhler ................ 351/38 |
| 4,431,279 A | 2/1984 | Morohashi ............ 351/245 |
| 4,790,647 A | 12/1988 | Mann et al. ........... 351/245 |
| 5,000,563 A | 3/1991 | Gisel et al. ........... 351/245 |
| 5,094,521 A * | 3/1992 | Jolson et al. .......... 351/210 |
| 5,125,731 A | 6/1992 | Fiorini et al. .......... 351/245 |
| 5,220,361 A | 6/1993 | Lehmer et al. ......... 351/226 |
| 5,387,952 A | 2/1995 | Byer ................... 351/208 |
| 5,491,757 A | 2/1996 | Lehmer et al. ......... 382/128 |
| 5,591,175 A | 1/1997 | Juto .................. 606/130 |
| 5,907,387 A | 5/1999 | Schwaegerle .......... 351/200 |
| 6,138,302 A * | 10/2000 | Sashin et al. .......... 5/600 |
| 6,220,706 B1 | 4/2001 | Foley ................. 351/209 |
| 6,481,848 B2 | 11/2002 | Hara et al. ........... 351/245 |
| 6,575,575 B2 | 6/2003 | O'Brien et al. ........ 351/245 |
| 2002/0159030 A1 | 10/2002 | Frey et al. ............ 351/212 |
| 2002/0169460 A1* | 11/2002 | Foster et al. .......... 606/130 |
| 2003/0160942 A1 | 8/2003 | Xie et al. ............. 351/205 |
| 2003/0160943 A1 | 8/2003 | Xie et al. ............. 351/209 |

FOREIGN PATENT DOCUMENTS

| EP | 0 045 897 A2 | 7/1981 |
| EP | 0 054 273 A1 | 12/1981 |
| EP | 0 242 723 A1 | 4/1987 |
| EP | 0 362 768 A1 | 10/1989 |

(Continued)

*Primary Examiner*—Jessica T Stultz
(74) *Attorney, Agent, or Firm*—Stallman & Pollock LLP

(57) ABSTRACT

A motorized head supporting and positioning apparatus is disclosed, such as is useful for eye examination or treatment. The apparatus includes head-receiving supports, which can include a forehead rest and a chinrest, which can be linked by a single arm assembly. A main assembly of the apparatus contains a motor assembly, which can include three motors driven in a coupled manner to guide a head along a three-dimensional path at a speed that is comfortable to the patient. The apparatus can be relatively compact, owing at least in part to a pivoted approximate Z-axis movement along the optical axis. In addition to open-loop operation, the apparatus can be used with a tracking subsystem to achieve closed-loop positioning in real time, as well as to enable the activation of an examination/treatment instrument when the eye is brought within an acceptable tolerance of a desired position.

43 Claims, 3 Drawing Sheets

FOREIGN PATENT DOCUMENTS

| | | |
|---|---|---|
| EP | 0 659 382 A2 | 10/1994 |
| GB | 268771 | 7/1927 |
| JP | 11-225958 | 8/1999 |
| WO | WO 00/13571 | 3/2000 |
| WO | WO 01/49223 A1 | 7/2001 |

* cited by examiner

MOTORIZED PATIENT SUPPORT FOR EYE EXAMINATION OR TREATMENT

TECHNICAL FIELD OF THE INVENTION

The present invention relates to head supporting and positioning apparatus and methods, such as may be useful for eye examination and/or treatment.

BACKGROUND

An apparatus for eye examination and treatment requires that a patient's eye be fixed in position with respect to the eye examination or treatment instrument. There is thus a need to initially and preliminarily position the patient head to approximately align the eye, and then to engage some fine adjustment to accurately align the selected eye (or both eyes) with the eye examination or treatment instrument.

Due to the fact that the head size and the relative position of the eye(s) with respect to the chin are different for different patients, it is necessary to adjust the head support to accommodate the various physical characteristics of a patient's head. Some prior art solutions are based on a relative positional adjustment of the chinrest with respect to the forehead rest, which could be followed by a positional adjustment of chinrest/forehead-rest assembly with respect to the eye examination/treatment instrument, or a positional adjustment of the eye examination/treatment instrument with respect to the assembly. Generally speaking, these movements are realized using manual adjustments (with the help of, for example, a joystick), which typically are inaccurate, repetitive, and time-consuming. Meanwhile, these movements also require a locking mechanism, or locking mechanisms, which typically require manual input from the operator to fix the relative position of the patient's head with respect to the instrument, which incurs more expense (see for example U.S. Pat. Nos. 3,594,072; 4,128,317; 4,139,280; 4,431,279; 4,790,647; 5,000,563; 5,125,731; 5,220,361; 5,907,387; 6,481,848; European Pat. No. EP 0054273; U.K. Patent No. 268,771; and PCT Pat. No. WO 01/49223, each of which is hereby incorporated herein by reference).

In spite of the fact that motorized movement may be more expensive, it can provide much better movement and positioning accuracy. At the same time, the need for locking the movable part(s) in position can be eliminated. When the motor stops at the correct position, the motor drive can be designed such that the movable part is locked in position. Existing references disclose such motorized movement, restricted to one- or two-dimensional movement of the patient support only (see, for example, U.S. Pat. No. 5,491,757 and Japanese Pat. No. JP11225958, hereby incorporated herein by reference), or to the three-dimensional movement of the eye examination/treatment instrument with respect to the chinrest/forehead rest assembly (see for example, U.S. Pat. Nos. 3,475,075; 5,907,387; and 6,575,575, hereby incorporated herein by reference).

Motorized movement of the eye examination/treatment instrument is typically more costly than motorized movement of the chinrest or forehead rest, due to the fact that the eye examination/treatment instrument typically has a multitude of cables that need to be routed between the moving parts of the instrument. A motorized eye examination/treatment instrument is also significantly bulkier due to the internal space requirement to accommodate the relative movement of the components. Moreover, conventional motorized mechanical systems generally are not very compact.

A major issue associated with eye examination or treatment is that a patient generally cannot maintain his or her head pressed against the chinrest and forehead rest, and hence fixed in position for a long time, due to fatigue, anxiety, loss of concentration, and other reasons. In general, an operator has to repeatedly discern whether the patient head is in position, and has to repeatedly remind the patient to reposition his or her head. This practice can be bothersome for both the operator and the patient, such that a solution is desired. Previous solutions have proposed that a headband is used to force the patient to fix his or her head to rest against the chinrest/forehead-rest assembly. This is, of course, intimidating and uncomfortable for the patient and is hence generally not practiced. The most recent solution is the use of sensors to give off a signal when the patient's head is moved away from the chinrest or forehead-rest, thereby automatically and politely reminding the patient to move his or her head back in position (see, for example, U.S. Pat. Nos. 5,387,952; 5,591,175; and PCT Pat. No. WO 00/13571, hereby incorporated herein by reference). One problem associated with these sensor based solutions is that, even though the patient is reminded to reposition his or her head back in contact with the chinrest and the forehead-rest, there is still no guarantee that his or her eye is in exactly the same original position as required.

BRIEF SUMMARY

Systems and methods in accordance with various embodiments of the present invention can overcome these and other deficiencies in existing head-positioning approaches. In one embodiment, a compact, motorized head supporting and positioning apparatus for eye examination and/or treatment is disclosed, which shall hereinafter be referred to as a Motorized Patient Support (MPS). An MPS apparatus can include head-receiving supports, such as a single-arm forehead rest and a chinrest, as well as a main assembly mounted with respect to an eye examination/treatment instrument, and a motor assembly, which can include a number of individual motors driven in a coupled manner, to guide the head of a patient to a desired position along any three-dimensional path. Various embodiments allow the three-dimensional movement to be performed at various speeds, in order to provide a level of comfort for the patient. While open-loop operation of the disclosed apparatus can be obtained using such a system, it can also be desirable to use a motorized patient support module with an eye tracking system to achieve closed-loop positioning or repositioning of an eye in real time.

In one aspect of an embodiment in accordance with the present invention, the forehead rest is linked to the corresponding base through a single arm assembly on one side of the to-be-positioned head. Unlike existing head positioning systems which utilize two arms, one on each side of the head, the use of a single arm provides open access to one side of the head, which is less confining and can be less intimidating for a patient when placing his or her head on the head rest assembly. It also can be easier for a doctor to visually check the eye level, as well as to manually manipulate an eyelid or an optical element positioned next to the eye. In addition, a forehead rest can be easily covered with a disposable slid-over plastic sleeve or other covering device for hygienic protection of the forehead rest, which would not be possible if an arm existed on both sides of the headrest.

Another aspect of one embodiment is to provide a motorized, three-dimensionally movable head support module. A unique feature of such an embodiment is the compactness of the head support module, which can be realized, for example, using a pivoted approximate longitudinal or Z-axis motion of the module with respect to the eye examination/treatment instrument. Owing to the fact that a pivoted Z-axis movement is not a true linear movement, a correction can be made through a compensating vertical or Y-axis movement. By coupling the motions of the motors of a motor module, such as a motor for each of the three axes, the head of the patient can be moved along a desired three-dimensional path at a speed, and with a smooth motion, that is comfortable to the patient.

Accordingly, an object of one embodiment is to operate the motorized head support module in an open loop fashion so that relatively fast and accurate automatic movement, as well as locking, of a patient head can be achieved. Such an open-loop operation can be beneficial for various applications. For example, the motor assembly can be programmed to re-center the eye when the eyeball is required to fixate on different targets that will result in a substantially predetermined displacement of the iris with respect to the optical axis of the eye examination/treatment instrument.

Another object of various embodiments is to combine the motorized patient head support with an eye tracking system, such that a true solution can be provided in terms of accurately positioning and maintaining an eye to a desired position. This can be achieved by obtaining an eye position signal from an eye tracking system and operating the motorized patient head support module in a closed-loop fashion, thereby constantly bringing back and maintaining the eye of the patient in a desired position. In addition, the eye examination/treatment instrument can be triggered to conduct the examination or the treatment when the eye is repositioned to within an acceptable tolerance of the desired position.

A further object of various embodiments is to make the motorized patient head support apparatus into a detachable module that can be easily attached to a series of different standardized eye examination/treatment instruments, such as autorefractors, fundus cameras, corneal topographers, OCT based eye imagers, eye wavefront sensors, laser eye surgery systems, and so on.

Still another object of various embodiments is to utilize a detachable chinrest that easily can be replaced. For instance a chinrest with a single chin cup could be replaced with a double chin cup or with angled chin cups, the latter for guiding the head of a patient into a position that does not match the gaze direction.

These and other features and advantages of the present invention will become more readily apparent to those skilled in the art upon review of the following detailed description of the preferred embodiments taken in conjunction with the accompanying drawings.

DETAILED DESCRIPTION

Systems and methods in accordance with various embodiments of the present invention can overcome deficiencies in existing head positioning systems by utilizing a motorized, three-dimensionally-movable patient head support. Such a support can be combined with an accurate eye tracking sensor system to provide a closed-loop system that, in real time, can constantly move the head of a patient back into position. Such a system also can take into consideration the fact that the patient can move his or her head while the head is being repositioned, such that there will be moments, or time durations, during which the eye of the patient is in the desired position. When this occurs, the eye examination/treatment instrument can be activated to conduct and/or complete the eye examination and/or treatment.

One embodiment in accordance with the present invention includes a compact motorized patient support (MPS) apparatus, which can be attached to an eye examination/treatment instrument. The MPS can be energized to accommodate various physical characteristics of an examination head, to move and fix the head, and hence the eye of interest, to a desired position. In addition, the MPS also can automatically re-adjust the eye back to the initial position if the patient has moved his or her head, or can reposition the eye to the original or other desired position(s) as required for eye examination and/or treatment.

An MPS apparatus in accordance with one embodiment can provide for the motorized three-dimensional movement of a head using at least one motor. In one embodiment, three motors are used, with one motor being used for each of the respective coordinate axes. It should be understood to one of ordinary skill in the art, however, that one or more motors can be used to drive the head support apparatus in three dimensions using any of a number of gears, pulleys, or other motion transfer mechanisms known and used in the art. Existing systems have used one or two motors to provide motion to a head support assembly, but only to provide movement in one or two dimensions. While a motor assembly in accordance with various embodiments can be driven to move a head in the X, Y, and Z directions of a Cartesian coordinate system using three motors independently, using a pivoted Z-axis motion can provide for the compactness of an MPS. By coupling a pivoted Z-axis motion with standard X- and Y-axis motions, a positioning action to move the patient head along any desirable three-dimensional path at a desired speed comfortable for the patient can be obtained. Such a compact design, together with other unique features of such a system, can bring about a number of advantages as described elsewhere herein.

Figure 1:
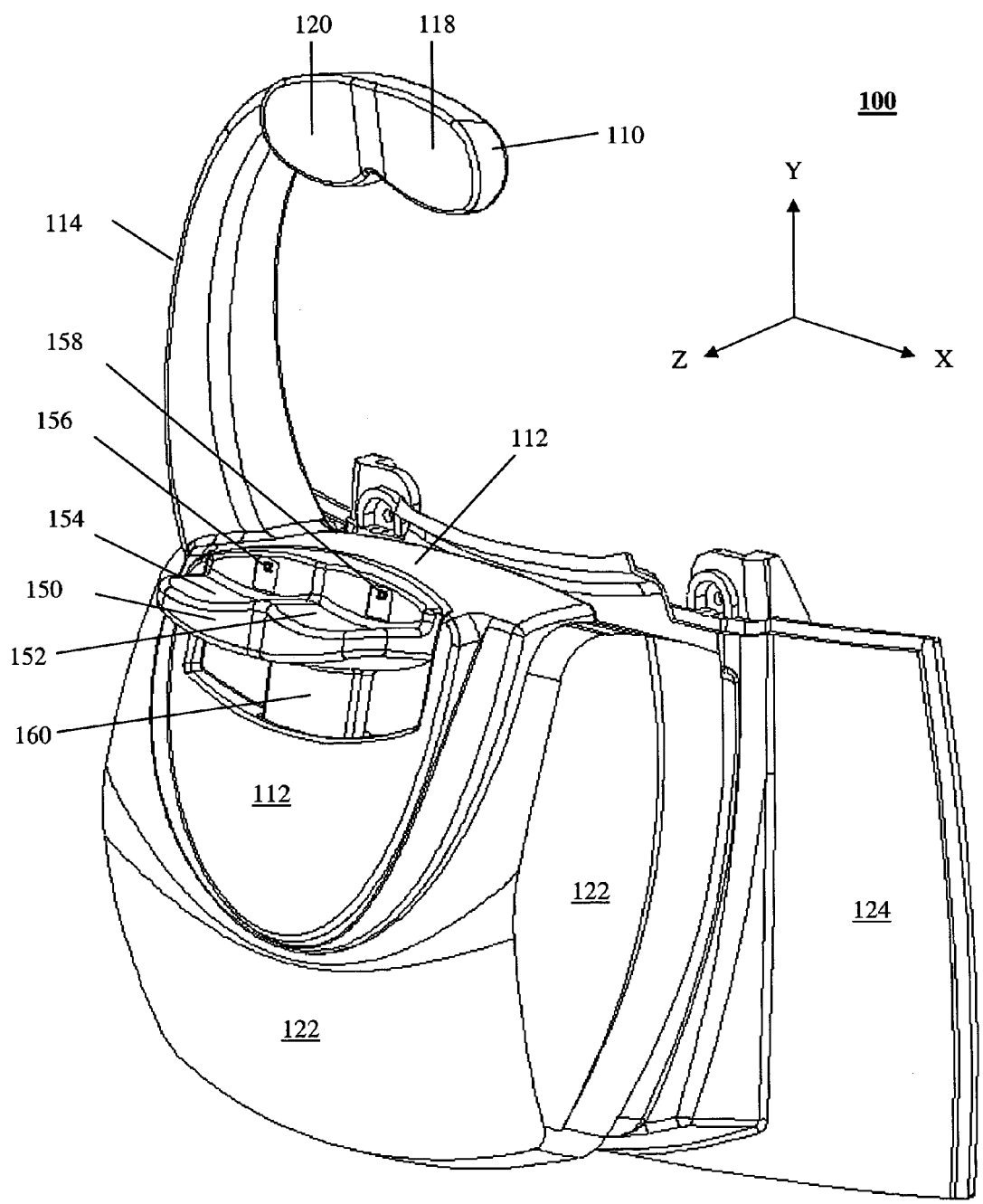
FIG. 1 shows a front side perspective view of a motorized patient support (MPS) module in accordance with one embodiment of the present invention.

FIG. 1 shows a front side perspective view of an MPS module 100 in accordance with one embodiment of the present invention. When in use, the MPS 100 can be attached to any of a series of different standardized examination/treatment instruments, such that motorized relative three-dimensional movement of the head of a patient, with respect to the parent instrument, can be realized. A forehead rest 110 and chinrest 150 provide two exemplary head-receiving supports that can contact, hold, and support the head of a patient. The chinrest 150 can have two chin cups 152 and 154, each serving for the preliminary positioning of one of the two eyes (left or right of the head). A primary benefit of having two chin cups is that the overall width of the MPS 100 can be reduced because the required lateral (i.e. in the X-axis direction) translation range for one eye with respect to the eye examination/treatment instrument is much less than that for both eyes at the same time. It should be understood, however, that many of the advantages of the various embodiments disclosed herein can be obtained using a device with a single chin cup or multiple chin cups, a single moveable chin cup, or other chin supports as known or used in the art. A sensor apparatus can be used for each chip cup, which in one embodiment consists of an illuminator (156 and 158) and a detector (on the surface of each chin cup but not visible in FIG. 1) to indicate whether a chin is present, such that the eye being examined/treated can be determined. While an optical sensor is illustrated here, it is to be understood that other sensors including capacitive, membrane contact, ultrasound, pressure, force, and other sensors, sensing systems, and sensing apparatus can also be used. It should also be understood that such a sensor also can serve to remind the patient to move his or her head back into position.

In FIG. 1, the chinrest 150 is linked to the forehead rest base 112 via a vertical chinrest support 160, which is constrained to move vertically (i.e. in the Y-axis direction) with respect to the forehead rest base 112. It should be noted that in one embodiment, the chinrest module, including the chinrest 150 and the chinrest support 160, is a detachable module that can be easily attached to the forehead rest base 112 for field replacement or servicing purposes. In the illustrated embodiment, the vertical movement of the chinrest 150 with respect to the forehead base 112 is a motorized movement that can serve two purposes at the same time, with the first one being the initial coarse adjustment of the eye level to cater for head size difference, and the second one being the fine adjustment that will be coupled with the other two directions to move or relocate the eye to a desired position. As will be elaborated later for a three motor system, both the Y motor and the Z motor may need to be activated in a coupled manner for strictly Z-axis movement in some embodiments, due to the fact that the Z-axis movement in some embodiments is pivoted, where the reference X-Y-Z coordinate system is that of the parent eye examination/treatment instrument. It should be pointed out that the vertical movement of the chinrest support 160 with respect to the forehead rest base 112 may also be a manual movement that is only used for the initial coarse adjustment of the eye level to cater for different head sizes. In such a case, the fine adjustment for the exact eye positioning can be achieved with a motorized vertical translation of the forehead rest base 112 together with the chinrest 150, such that the chinrest and the forehead rest can be moved up and down together.

A forehead rest module can comprise the forehead rest 110, a single arm 114, and a forehead rest base 112. In one embodiment, the forehead rest 110 has two headrest indentations 118 and 120, which correspond to the two chin cups 152 and 154, for preliminary positioning of one of the two eyes. However, a single forehead rest indentation to be used with two chin cups or a single forehead rest indentation to be used with only one chin cup could also be a design choice.

While it is not absolutely necessary for a forehead rest to have any sensors or sensing apparatus, sensors can be incorporated into each forehead rest indentation to indicate whether a forehead is present, as well as which eye is being examined/treated, and/or to remind the patient to move his or her forehead back in position. As in the case of the chin cup sensor, the sensor for the forehead rest can be an optical sensor in which case an illuminator and a detector pair may be used. It is to be understood that other sensors, sensing apparatus, and sensing means can be used, including capacitive, membrane contact, ultrasound, pressure, and force sensors and sensing systems. In addition to standard chin cups as known and used in the art, angled dual chin cups can be provided to guide a head into position that does not match the gaze direction. This can be beneficial, for example, when a Placido disk device is used where the nose can interfere with the measurement. In such a case, it may be beneficial to use a single forehead rest indentation, rather than dual forehead rest indentations.

Systems and methods in accordance with various embodiments also can overcome various deficiencies in existing head support devices by utilizing a curved, shaped, or bent single arm 114, instead of two arms as in existing devices, to link a forehead rest 110 to a forehead rest base 112, and hence a chinrest 150 or other head-receiving support. When using a single arm instead of two arms, a patient can feel less confined and intimidated. An added benefit of using a single arm is the ease with which a doctor can visually check the initial level of the patient head relative to the parent instrument from the open side. The doctor also can more easily manipulate the head, including any anatomical features such as the eyelid or any optical elements that are to be positioned next to the eye to be examined, without any visual or physical obstruction from the open side. Another benefit is the ability to cover the forehead rest 110 with a disposable thin plastic sleeve or other temporary cover in order to easily maintain the forehead rest 110 free from dirt or sweat, such that for each patient a new sleeve can be slid over the forehead rest for hygiene reasons.

In an embodiment such as is shown in FIG. 1, a forehead rest base 112 together with a forehead rest 110 and single arm 114 can be automatically movable when driven by a motor assembly in the lateral or X-axis direction with respect to the main assembly 122. The main assembly 122 can be pivoted at the bottom with respect to the instrument interface panel 124, can be driven, such as by a Z-motor of the motor assembly, to move in approximately the Z-axis direction. As mentioned before, if a true Z-axis movement is desired, a Z-motor or Z-motion component can be coupled with a Y-motor or Y-motion component to compensate for the Y-axis movement introduced purely by the pivoted approximate Z-movement.

The MPS can include an easily detachable module that can be attached to a variety of standardized eye examination/treatment instruments. In this respect, the instrument interface panel 124 can be a part of the parent instrument, in which case a Z-motor component and the pivot portion of the main assembly can be mounted onto the parent instrument. On the other hand, the instrument interface panel 124 can be a part of the MPS module, in which case the panel 124 can be mounted onto the parent instrument.

Figure 2:
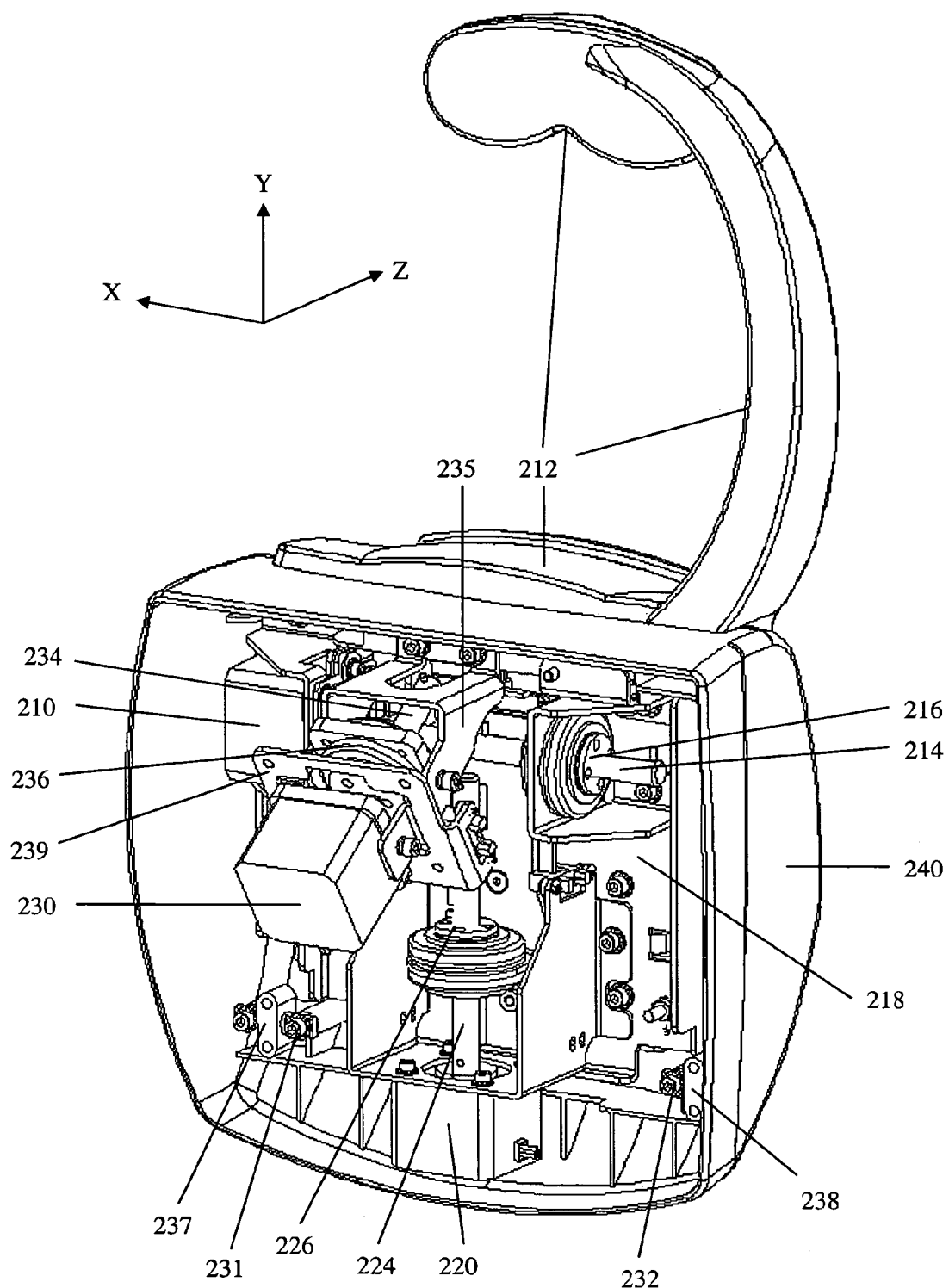
FIG. 2 shows a backside perspective view of the MPS module of FIG. 1 with the instrument interface panel removed to reveal some of the details inside the MPS module.

FIG. 2 shows a backside perspective view of the MPS module of FIG. 1 with the instrument interface panel removed to reveal some of the details inside the MPS module. In this embodiment, which utilizes a separate motor in the motor assembly for each axis, the X-motor body 210 is directly mounted on the main assembly 240. The X-motor lead screw 214 is connected to the X driver nut 216 that is attached to the forehead mounting plate 218. As a result, when the X-motor is activated to rotate in one angular direction or the other, the lead screw 214 will rotate and will move the X driver nut 216 to the left or right, causing the forehead mounting plate 218 and therefore the forehead rest base 212 to move in the X-direction.

The Y-motor body 220 is attached to the forehead mounting plate 218 and the Y-motor lead screw 224 is connected to the Y driver nut 226 that is attached to the chinrest support. As a result, when the Y-motor is energized to rotate in one angular direction or the other, the Y lead screw 224 will rotate to cause the Y driver nut 226 and hence the chinrest support to move up and down with respect to the forehead mounting plate 218. Activation of the X-motor will move the forehead rest, which will carry the chinrest, since the Y-motor body 220 and hence the chinrest module is attached to forehead mounting plate 218. The Z-motor body 230 is mounted via a U bracket 239 to the instrument interface panel, which in turn mounts to the two pivot bushings 237 and 238 that can rotate around central shafts 231/232 rigidly mounted onto the main assembly 240.

The Z-motor lead screw 234 is connected to the Z driver nut 236, but the Z-driver nut 236 is pivoted to a U bracket 235 that is rigidly connected to the main assembly 240. This pivoting of the Z-motor drive nut 236 with respect to the U bracket 235 can be required in this embodiment due to the relative angular movement between the Z driver nut 236 and the Z-motor lead screw 234, owing to the pivoting action of the bushings 237 and 238. For a similar reason, the Z-motor body 230 can be pivoted relative to U bracket 239. When the Z-motor is activated, the Z lead screw 234 will rotate in one angular direction or the other, in order to move the Z driver nut 236 back and forth with respect to the Z motor body 230. Due to the pivoting at the position of the two pivot bushings 237 and 238, the main assembly 240 may only approximately, rather than strictly linearly, move in and out with respect to the instrument interface panel in the Z-direction. As mentioned before, this approximate Z-axis movement can be corrected by a coordinated activation of the Z-motor and the Y-motor to create a true Z-axis motion. Furthermore, by coordinating the activation of all three motors in this embodiment, any desired movement of the patient head with respect to the parent instrument along any desired three-dimensional path and at a speed comfortable to the patient may be achieved.

A position sensor can be used to measure the movement along each axis, as driven by each motor, and a translation range limit. A home position also can be established for each motor in the motor assembly, such that an MPS can be programmed to stop at the range limits and to return to its home position as desired. If using a stepper motor, a home position sensor alone can be used on each axis which, coupled with motor step count, can measure position and range limits.

While FIG. 2 only shows one embodiment in terms of mounting the motors, it should be understood that there can be many other approaches to mounting the motors in order to achieve the same goal of moving the patient head in three dimensions in a controlled manner. This coordinated movement can be achieved by means of an electronic joystick, or pre-programmed keys that drive two or more motors at similar or different speeds. These variations should be obvious within the spirit and scope of the present invention.

Figure 3:
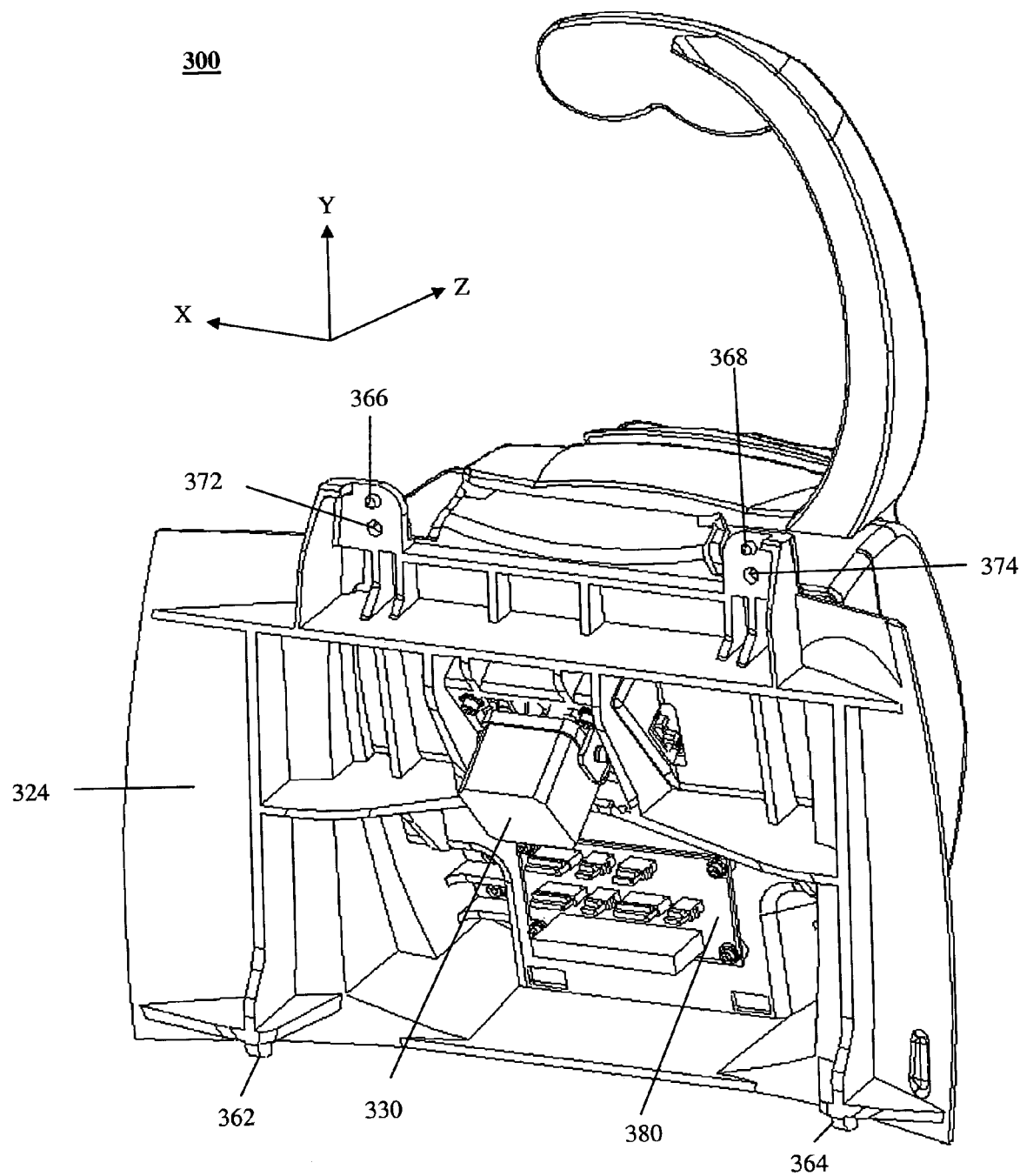
FIG. 3 shows a backside perspective view of the MPS module of FIG. 1.

FIG. 3 shows the backside perspective view of an exemplary MPS module with the instrument interface panel 324 being attached to the main assembly. As mentioned before, an MPS module as shown in FIG. 2 can be considered as an independent detachable sub-assembly for attachment to a series of standardized parent instrument, as well as for field servicing. There, the Z-motor body and the two pivot bushings can be connected to the parent instrument together with electrical connections for the motors, as well as any position sensors. An MPS module as shown in FIG. 3 also can be considered to be an independent replaceable unit. Here, the Z-motor body 330 and the two pivot bushings (not visible in FIG. 3) have already been rigidly mounted and connected with the instrument interface panel 324, which will in turn need to be connected both mechanically and electrically with the parent instrument. In this illustrated embodiment, the mechanical connection can be obtained by engaging and locating the interface panel 324 via four engaging/locating features 362, 364, 366, and 368, as well as by screwing the interface panel 324 onto the parent instrument through two screw holes 372 and 374. The screws can be replaced with snap features or other fastening devices known or used in the art. The electrical connection can be achieved with the aid of an electrical connection panel 380.

A motorized patient support (MPS) can be programmed to position an eye in an open loop manner for various applications. In one example, a camera is used with the measurement method, and the eye is positioned relative to a cross-hair by actuating the MPS X and Y motors. The MPS can be used to refocus the camera image in a similar way by activating the Z-motor with coupled Y motor correction. Such a camera is only an example of many eye position measurement devices that can be used with various embodiments. In another example, an MPS can be used to re-center the eye when the eye is provided with fixation targets that deviate from one another. In such a case, even if the eye is viewing off-axis, there typically is a requirement for the pupil to be nominally centered on the optical axis. Owing to the swiveling of the eyeball in its socket, there can be a displacement of the pupil relative to the instrument when different fixation targets are viewed. From human factors, this displacement can be calculated and corrected for using an MPS in accordance with various embodiments.

In addition to open loop operation, an MPS in accordance with various embodiments can be used in combination with an eye-tracking system that enables closed-loop operation, whereby the MPS can constantly reposition the eye to a desired position in real time. In this case, the eye tracking system can provide a feedback signal based on information from any, or all, of the different focal planes in the eye, including the retina, lens, and cornea. For example, the eye tracking system can be based on tracking the corneal vertex using two off-axis radiation emitter-photodetector pairs, such as is disclosed in U.S. Pat. No. 6,220,706, or a more general eye tracking system that can be used to track not only the cornea but also the retina, lens, or other feature in the eye, such as is disclosed in U.S. Pat. Application Document Nos. 2003/0160942 and 2003/0160943, wherein a tracking beam of radiation is scanned onto a region of interest in the eye that has a reference-tracking feature and hence can provide a feedback signal.

An MPS module in accordance with various embodiments can be used with a large variety of examination/treatment instruments, where there is a need for a precise alignment between such an instrument and the head of a patient. Exemplary instruments include autorefractors, fundus cameras, corneal topographers, OCT based eye imagers, eye wavefront sensors, laser eye surgery systems, visual field analyzers, and so on, including many instruments not directly related to examining or treating the eye of a patient. Meanwhile, there are also a number of other advantageous features of the presently invented MPS. For example, there are no pinch points for both patient and operator safety; the MPS can be marketed as a stand-alone module; the MPS is designed for aesthetics; its smooth and quiet operation is ideal for medical environments; and it is easy to assemble.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

What is claimed is:

1. A motorized, three-dimensional patient head supporting and positioning apparatus, comprising:
   first and second head-receiving supports for contacting the head of a patient; and
   a motor assembly coupled to the first and second head-receiving supports and capable of moving the head-receiving supports in order to guide the head in three dimensional space and wherein the motor assembly contains a plurality of motors driven in a coordinated way in order to provide movement in any direction and at an overall movement speed that is comfortable to a patient.

2. An apparatus according to claim 1, wherein:
the motor assembly contains three motors that can be driven in a coupled manner to provide three-axis motion of the first and second head-receiving supports.

3. An apparatus according to claim 1, wherein:
the first head-receiving support is a forehead rest.

4. An apparatus according to claim 1, wherein:
the second head-receiving support is a chin rest.

5. An apparatus according to claim 4, wherein:
said chin rest has two chin cups, each cup being positioned to support the head for one eye of the head, such that a lateral translation range of said motor assembly is reduced.

6. An apparatus according to claim 1, wherein:
at least one of the first and second head-receiving supports includes a sensor device for indicating whether a head is in proximate contact with said head-receiving supports.

7. An apparatus according to claim 6, wherein:
the sensor device is selected from the group consisting of illuminator/photodetector sensors, membrane contact switches, pressure switches, spring force switches, capacitive coupling sensors, and ultrasound sensors.

8. An apparatus according to claim 4, wherein:
the chin rest includes at least one chin cup that is angled for easy guiding of the head into a position that does not match the gaze direction.

9. An apparatus according to claim 1, wherein:
the motor assembly includes a Y-axis drive motor for moving at least one of the head-receiving supports along a Y-axis direction in order to guide the head along the Y-axis direction.

10. An apparatus according to claim 1, wherein:
the motor assembly includes an X-axis drive motor for moving the first and second head-receiving supports along an X-axis direction in order to guide the head along the X-axis direction.

11. An apparatus according to claim 1, wherein:
the motor assembly includes a Z-axis drive motor for moving the first and second head-receiving supports along a Z-axis direction in order to guide the head along the Z-axis direction.

12. An apparatus according to claim 1, further comprising:
a main assembly containing the motor assembly and for mounting the first and second head-receiving supports.

13. An apparatus according to claim 1, wherein:
the motor assembly provides a pivoted Z-direction movement of the first and second head-receiving supports.

14. An apparatus according to claim 13, wherein:
the motor assembly adjusts for the pivoted Z-direction movement by generating a compensating movement along a Y-axis direction, in order to cause a substantially linear motion of the first and second head-receiving supports along a Z-axis direction.

15. An apparatus according to claim 1, further comprising:
a user controllable input device for controlling the speed of movement of the motor assembly.

16. An apparatus according to claim 1, wherein:
the motor assembly is capable of guiding the head such that the pupil of an eye of the head is re-centered when the eye moves to fixate on a target.

17. An apparatus according to claim 1, wherein:
at least one of the first and second head-receiving supports is detachable.

18. An apparatus according to claim 1, wherein:
the apparatus is capable of being attached to any of a number of standardized examination/treatment instruments, including instruments selected from the group consisting of autorefractors, fundus cameras, corneal topographers, OCT based eye imagers, eye wavefront sensors, laser eye surgery systems, and visual field analyzers.

19. A method for guiding a head of a patient to a desired position, comprising the steps of:
placing the head of a patient in contact with first and second head-receiving supports;
controlling a motor assembly to move the first and second head-receiving supports in order to guide the head in any of three axes to a desired position; and
controlling the speed of the motor assembly in order to provide an overall movement speed that is comfortable to the patient.

20. A method according to claim 19, further comprising:
using at least one sensor to indicate whether a head is in proximate contact with said one of said first and second head-receiving supports.

21. A method according to claim 19, wherein:
moving one of the first and second head-receiving supports along a Y-axis in order to guide the head along the Y-axis direction before moving the first and second head-receiving supports in the X- and Z-axis directions.

22. A method according to claim 19, further comprising:
guiding the head such that an eye of the head is re-centered when the eye moves to fixate on a target.

23. A method according to claim 19, further comprising:
positioning a removable sleeve over at least a portion of the first head-receiving support in order to form a barrier between the patient head and the first head-receiving support.

24. A motorized patient head support apparatus for positioning the head with respect to an examination or treatment device in three dimensional space defined by an X/Y plane spaced a distance Z from the device, said apparatus comprising:
a head receiving support structure including an independently movable chinrest;
a first motor assembly including a first linear drive directed substantially along a first axis;
a second motor assembly including a second linear drive directed substantially along a second axis, said second linear drive begin coupled to said chin rest for linearly moving the chin rest independent of the support structure; and
a third motor assembly including a third linear drive directed substantially along a third axis, said drives being coupled to said head receiving support structure in order to guide the head substantially linearly in three dimensional space.

25. An apparatus as recited in claim 24, wherein said second linear drive moves said chin rest substantially along the Y-axis.

26. An apparatus as recited in claim 25, wherein said support structure further includes a base which carries said chin rest and is independently movable with respect to the support structure, and wherein said first linear drive is coupled to said base for linearly moving said base and said chin rest substantially along the X-axis.

27. An apparatus as recited in claim 26, wherein said base carries a forehead rest.

28. An apparatus as recited in claim 27, wherein actuation of the third linear drive induces pivotal motion of the base to approximate motion in the Z-axis.

29. An apparatus as recited in claim 28, wherein the approximate motion in the Z-axis is corrected to create true Z-axis motion of the head by actuation of the second linear drive.

30. An apparatus as recited in claim 24, wherein first, second and third motor assemblies are driven in a coordinated way in order to provide movement in any direction and at an overall movement speed that is comfortable to a patient.

31. An apparatus as recited in claim 24, further including a user controllable input device for controlling the first, second and third motor assemblies.

32. An apparatus as recited in claim 24, wherein actuation of the third linear drive induces pivotal motion of the head receiving support structure to approximate motion along the third axis.

33. An apparatus as recited in claim 32, wherein the approximate motion along the third axis is corrected to create true third axis motion of the head by actuation of the second linear drive.

34. A motorized patient head support apparatus for positioning the head with respect to an examination or treatment device in three dimensional space defined by an X/Y plane spaced a distance Z from the device, said apparatus comprising:
   a base carrying a forehead rest;
   a chin rest carried by said base;
   a first motor assembly for linearly driving the chin rest with respect to the base and the forehead rest substantially in the Y-axis;
   a second motor assembly for linearly driving the base and the chin rest substantially in the X-axis; and
   a third motor assembly for driving the base and the chin rest substantially in the Z-axis.

35. An apparatus as recited in claim 34, wherein said third motor assembly drives the base and the chin rest about a pivot to approximate the motion in the Z-axis.

36. An apparatus as recited in claim 35, wherein the approximate motion in the Z-axis is corrected to create true Z-axis motion of the head by actuation of the first motor assembly.

37. An apparatus as recited in claim 34, wherein first, second and third motor assemblies are driven in a coordinated way in order to provide movement in any direction and at an overall movement speed that is comfortable to a patient.

38. An apparatus as recited in claim 34, further including a user controllable input device for controlling the first, second and third motor assemblies.

39. A motorized patient head support apparatus for positioning the head with respect to an examination or treatment device in three dimensional space defined by an X/Y plane spaced a distance Z from the device, said apparatus comprising:
   a first support module carrying a first head receiving support;
   a second support module carrying a second head receiving support, said second support module being carried by said first support module and being independently movable with respect thereto;
   a first motor assembly for linearly driving the first support module substantially along a first axis;
   a second motor assembly for linearly driving the second support module substantially along a second axis independent of the first support module; and
   a third motor assembly for driving the second support module substantially along a third axis to guide the head in three dimensional space.

40. An apparatus as recited in claim 39, wherein said third motor assembly drives said second support module about a pivot to approximate the motion along the third axis.

41. An apparatus as recited in claim 40, wherein the approximate motion along the third axis is corrected to create true third axis motion of the head by actuation of the first motor assembly.

42. A motorized patient head support apparatus for positioning the head with respect to an examination or treatment device in three dimensional space defined by an X/Y plane spaced a distance Z from the device, said apparatus comprising:
   a head receiving support structure;
   a first motor assembly including a first linear drive directed substantially along a first axis;
   a second motor assembly including a second linear drive directed substantially along a second axis; and
   a third motor assembly including a third linear drive directed substantially along a third axis, said drives being coupled to said head receiving support structure in order to guide the head substantially linearly in three dimensional space and wherein actuation of the third linear drive induces pivotal motion of the head receiving support structure to approximate motion along the third axis and wherein the approximate motion along the third axis is corrected to create true third axis motion of the head by actuation of the second linear drive.

43. A motorized patient head support apparatus for positioning the head with respect to an examination or treatment device in three dimensional space defined by an X/Y plane spaced a distance Z from the device, said apparatus comprising:
   a first support module carrying a first head receiving support;
   a second support module carrying a second head receiving support;
   a first motor assembly for linearly driving the first support module substantially along a first axis;
   a second motor assembly for linearly driving the second support module substantially along a second axis; and
   a third motor assembly for driving the second support module about a pivot to approximate the motion along a third axis wherein the approximate motion along the third axis is corrected to create true third axis motion of the head by actuation of the first motor assembly.

* * * * *